(12) United States Patent
Huang et al.

(10) Patent No.: US 11,766,299 B2
(45) Date of Patent: Sep. 26, 2023

(54) METHOD AND SYSTEM FOR REGISTER OPERATING SPACE

(71) Applicant: METAL INDUSTRIES RESEARCH & DEVELOPMENT CENTRE, Kaohsiung (TW)

(72) Inventors: Bing-Feng Huang, Kaohsiung (TW); Jin-Yuan Syue, Tainan (TW); Chih-Lung Lin, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 416 days.

(21) Appl. No.: 17/128,174

(22) Filed: Dec. 20, 2020

(65) Prior Publication Data

US 2022/0192762 A1    Jun. 23, 2022

(51) Int. Cl.
| | |
|---|---|
| *A61B 34/30* | (2016.01) |
| *A61B 34/00* | (2016.01) |
| *A61B 34/20* | (2016.01) |
| *A61F 5/02* | (2006.01) |
| *A61B 90/00* | (2016.01) |

(52) U.S. Cl.
CPC .............. *A61B 34/25* (2016.02); *A61B 34/20* (2016.02); *A61B 34/30* (2016.02); *A61B 90/37* (2016.02); *A61F 5/028* (2013.01); *A61B 2034/303* (2016.02); *A61B 2090/3762* (2016.02); *A61B 2090/3983* (2016.02)

(58) Field of Classification Search
CPC ......... A61B 34/00; A61B 34/20; A61B 34/30; A61B 34/25; A61B 90/00; A61B 90/37; A61B 19/201; A61B 19/5244; A61B 2019/208
See application file for complete search history.

(56) References Cited

U.S. PATENT DOCUMENTS

| | | | |
|---|---|---|---|
| 4,691,696 A | * | 9/1987 | Farfan de los Godos ................... A61F 5/028 128/95.1 |
| 6,351,659 B1 | | 2/2002 | Vilsmeier |
| 9,125,680 B2 | | 9/2015 | Kostrzewski et al. |

(Continued)

FOREIGN PATENT DOCUMENTS

| | | |
|---|---|---|
| EP | 2211749 B1 | 10/2018 |
| TW | 381008 B | 2/2000 |

(Continued)

*Primary Examiner* — Vi X Nguyen
(74) *Attorney, Agent, or Firm* — CKC & Partners Co., LLC

(57) ABSTRACT

A system for registering operating space includes a back bracing, a computer system and a robotic arm. The back bracing includes positioning marks which can be imaged in a computer tomography (CT) image, and the back bracing is used to be worn by a patient. The computer system computes image coordinates of the positioning marks in an image space. A base of the robotic arm is connected to the back bracing in an operating space after the CT image is generated. The robotic arm contacts the positioning marks in the operating space and meanwhile the computer system obtains arm coordinates of the robotic arm in an arm space. The computer system generates conversion models among the image space, the operating space, and the robot arm space according to the image coordinates and the arm coordinates.

5 Claims, 5 Drawing Sheets

(56) References Cited

U.S. PATENT DOCUMENTS

| | | |
|---|---|---|
| 9,713,499 B2 | 7/2017 | Bar et al. |
| 10,182,872 B2 | 1/2019 | Chang et al. |
| 2007/0270660 A1 | 11/2007 | Caylor, III et al. |
| 2017/0095299 A1* | 4/2017 | Hendrick ................ A61B 34/30 |
| 2017/0189219 A1* | 7/2017 | Jensen .................. A61F 2/4455 |
| 2018/0092699 A1 | 4/2018 | Finley |
| 2019/0167356 A1 | 6/2019 | Britton et al. |

FOREIGN PATENT DOCUMENTS

| | | |
|---|---|---|
| TW | I572316 B | 3/2017 |
| TW | I586327 B | 6/2017 |
| TW | I605789 B | 11/2017 |
| WO | 2018075784 A1 | 4/2018 |
| WO | 2020163328 A1 | 8/2020 |

* cited by examiner

METHOD AND SYSTEM FOR REGISTER OPERATING SPACE

BACKGROUND

Field of Invention

The present disclosure relates to a system and a method for registering an operating space, an image space and an arm space.

Description of Related Art

With the increase of aging population and the influence of modern life characteristics such as obesity, sedentary, etc., diseases of spine lesions are increasing year by year. If conservative treatment fails, it is often necessary to rely on implants to reduce pain and maintain basic functions. The spine is responsible for protecting the central nervous system, but the portion where the implants that can be applied are quite narrow. For example, a pedicle screw may damage the central nervous system. Although an orthopedic minimally invasive surgery is available in the market, how to accurately track the position of the spine during the surgery is still an issue since the position of the spine changes with the patient's posture.

SUMMARY

Embodiments of the present disclosure provide a system for registering operating space. The system includes a back bracing, a computer system and a robotic arm. The back bracing includes positioning marks which are configured to be imaged in a computer tomography image. The back bracing is configured to be worn by a patient. The computer system is configured to recognize the positioning marks in the computer tomography image and compute image coordinates of the positioning marks in an image space. The robotic arm includes a base which is configured to connect to the back bracing in an operating space after the computer tomography image is generated. The robotic arm is configured to contact the positioning marks in the operating space, and the computer system is configured to obtain arm coordinates in an arm space when the robotic arm contacts the positioning marks. The computer system is further configured to generate at least one conversion model among the image space, the operating space, and the arm space according to the image coordinates and the arm coordinates.

In some embodiments, the back bracing includes straps which are configured to be tied onto a body portion the patient, and each of the positioning marks is disposed on one of the straps.

In some embodiments, the back bracing further includes a rigid structure configured to connect to the base.

In some embodiments, the computer system is configured to provide a navigation interface, transform a real-time arm position of the robotic arm in the arm space into a real-time image position in the image space based on the at least one conversion model, and renders a virtual object of the robotic arm in the navigation interface according to the real-time image position.

In some embodiments, the system further includes a camera, a spine positioning mark, and an arm positioning mark. The spine positioning mark is configured to be fixed on a spine of the patient, and the arm positioning mark is configured to be fixed on the robotic arm. The camera is configured to capture an image, and the computer system is configured to recognize the spine positioning mark and the arm positioning mark in the image to compute a position of the robotic arm relative to the spine positioning mark in the operating space.

From another aspect, a method for registering operating space is provided. The method includes: obtaining a computer tomography image, recognizing positioning marks in the computer tomography image and computing image coordinates of the positioning marks in an image space, in which the positioning marks are disposed on a back bracing which is configured to be worn by a patient; controlling a robotic arm to contact the positioning marks in an operating space, and obtaining arm coordinates in an arm space when the robotic arm contacts the positioning marks, in which the robotic arm includes a base which is configured to connect to the back bracing in the operating space after the computer tomography image is generated and before the robotic arm contacts the positioning marks; and generating at least one conversion model among the image space, the operating space, and the arm space according to the image coordinates and the arm coordinates.

In some embodiments, the method further includes: provide a navigation interface; transforming a real-time arm position of the robotic arm in the arm space into a real-time image position in the image space based on the at least one conversion model; rendering a virtual object of the robotic arm in the navigation interface according to the real-time image position.

In some embodiment, a spine positioning mark is configured to be fixed on a spine of the patient, and an arm positioning mark is configured to be fixed on the robotic arm. The method further includes: capturing, by a camera, an image; and recognizing the spine positioning mark and the arm positioning mark in the image to compute a position of the robotic arm relative to the spine positioning mark in the operating space.

In the aforementioned system and method, the process for registering spaces is simplified by using the back bracing.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence. In addition, the term "couple" used in the specification should be understood for electrically connecting two units directly or indirectly. In other words, when "a first object is coupled to a second object" is written in the specification, it means another object may be disposed between the first object and the second object.

A system for registering an operating space is provided. The system includes a computer system, a robotic arm, and a back bracing which is worn by a patient. The back bracing includes multiple positioning marks. Conversion models among different spaces can be computed quickly by an approach which will be described in detail below.

Figure 1:
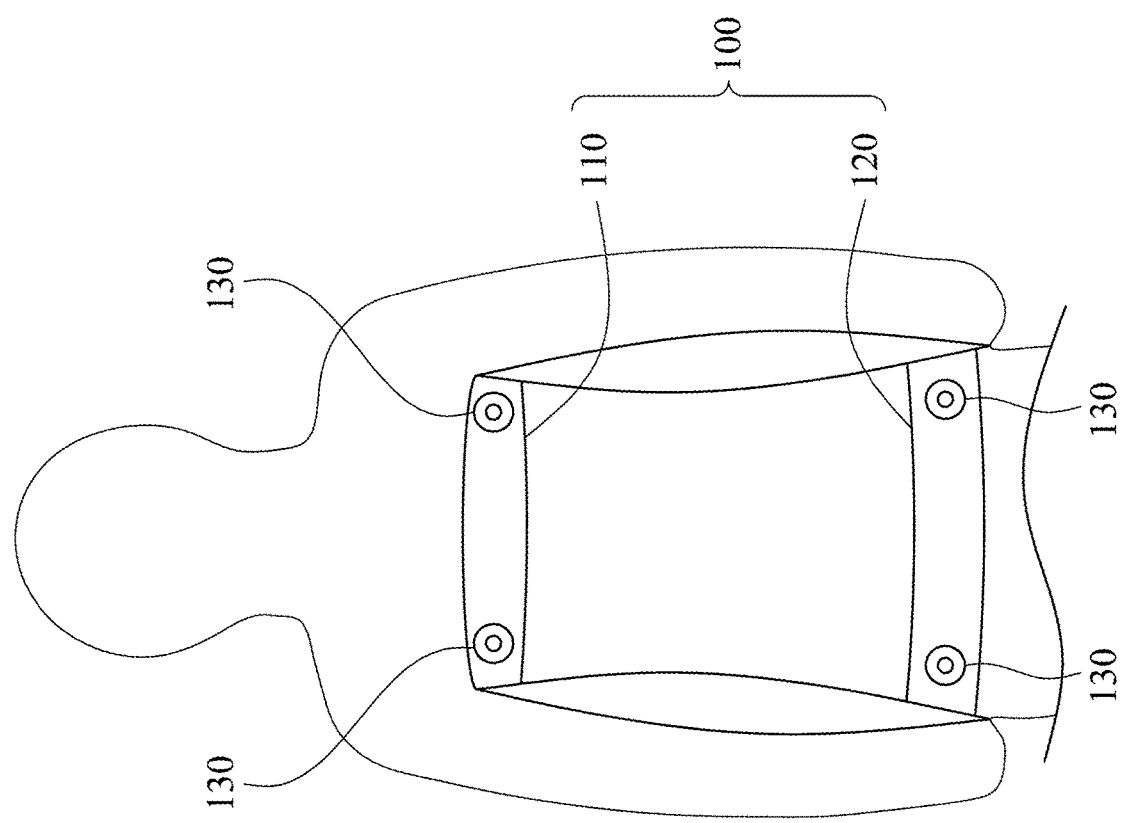
FIG. 1 is a schematic diagram of a back bracing in accordance with an embodiment.
Figure 2:
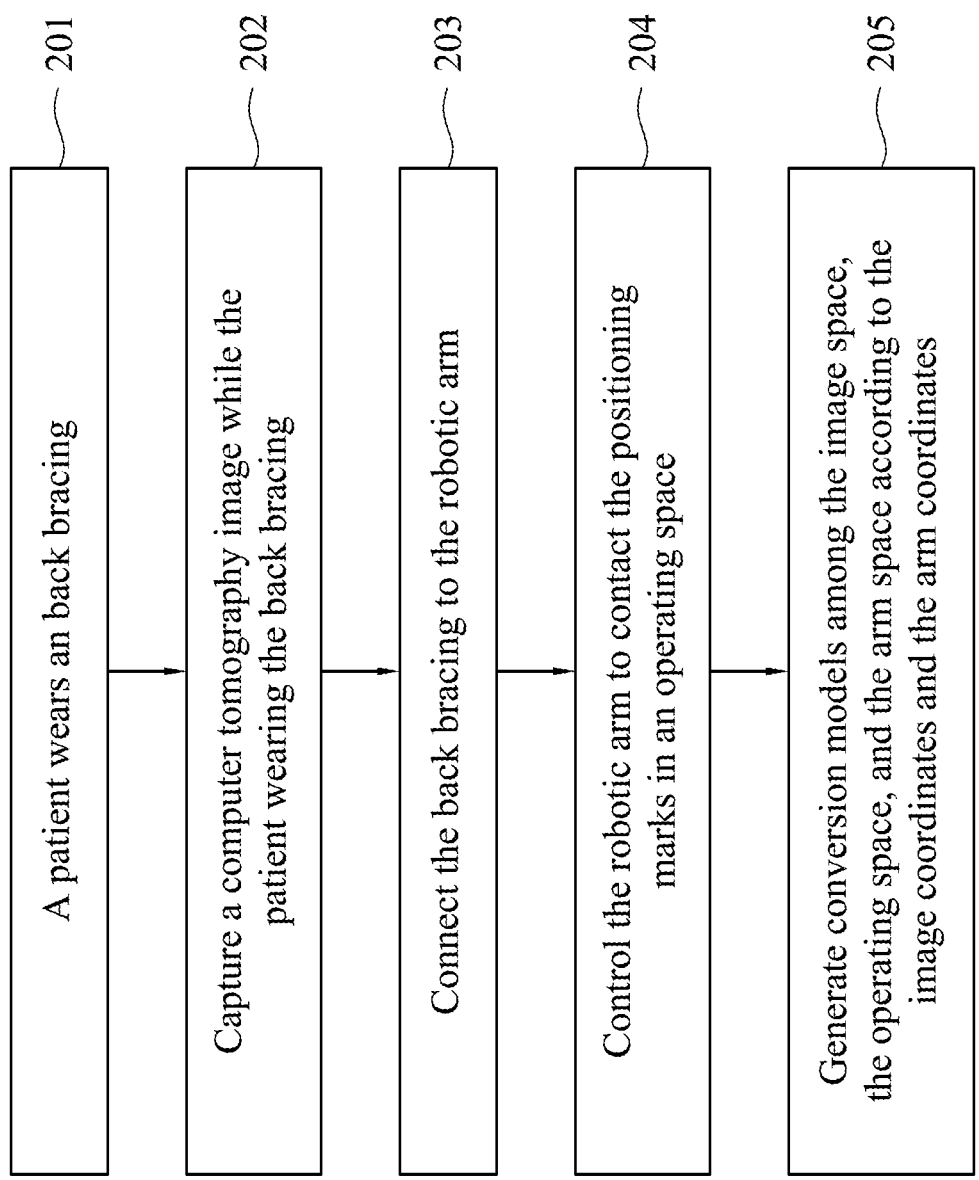
FIG. 2 is a flow chart of a method for registering an operating space in accordance with an embodiment.

FIG. 1 is a schematic diagram of a back bracing in accordance with an embodiment. FIG. 2 is a flow chart of a method for registering an operating space in accordance with an embodiment. Referring to FIG. 1 and FIG. 2, in step 201, a back bracing 100 is worn by a patient. In the embodiment of FIG. 1, the back bracing 100 includes straps 110 and 120 which are tied onto the patent. The straps 110 and 120 are tied onto the body portion of the patient in the embodiment, but they may be tied onto limbs or other portions of the patent. Several positioning marks 130 are disposed on the straps 110 and 120. The material of the positioning marks 130 includes, for example, material which can be imaged in a computer tomography (CT) image. The positioning marks 130 locate at four corner of the body to prevent from masking the spine of the patent in the CT image. However, the back bracing 100 shown in FIG. 1 is merely an example, and the back bracing 100 may have any suitable material, shape and/or structure as needed. The number and positions of the positioning marks 130 are not limited in the disclosure. After the patient wears the back bracing 100, the positions of the positioning marks 130 relative to the patient is fixed. In some embodiments, the back bracing 100 has a rigid frame to help support or fix the spine of the patient. In some embodiments, the back bracing 100 is deformable such that the positions of the positioning marks 130 change along with the patient's posture. In other words, the position of the spine can be computed by detecting the positions of the positioning marks 130.

In step 202, a computer tomography image is captured while the patient wearing the back bracing. The computer system recognizes the positioning marks 130 in the CT image to compute image coordinates of each of the positioning marks 130 in an image space. The image coordinates are represented as a vector X. Herein, the computer system can recognize the positioning marks 130 by any image processing algorithms or computer vision approaches. For example, the shape of the positioning marks 130 is known, and therefore the computer system can search the positioning marks in the CT image based on a preset pattern and record the positions of the positioning marks as the image coordinates.

Figure 3:
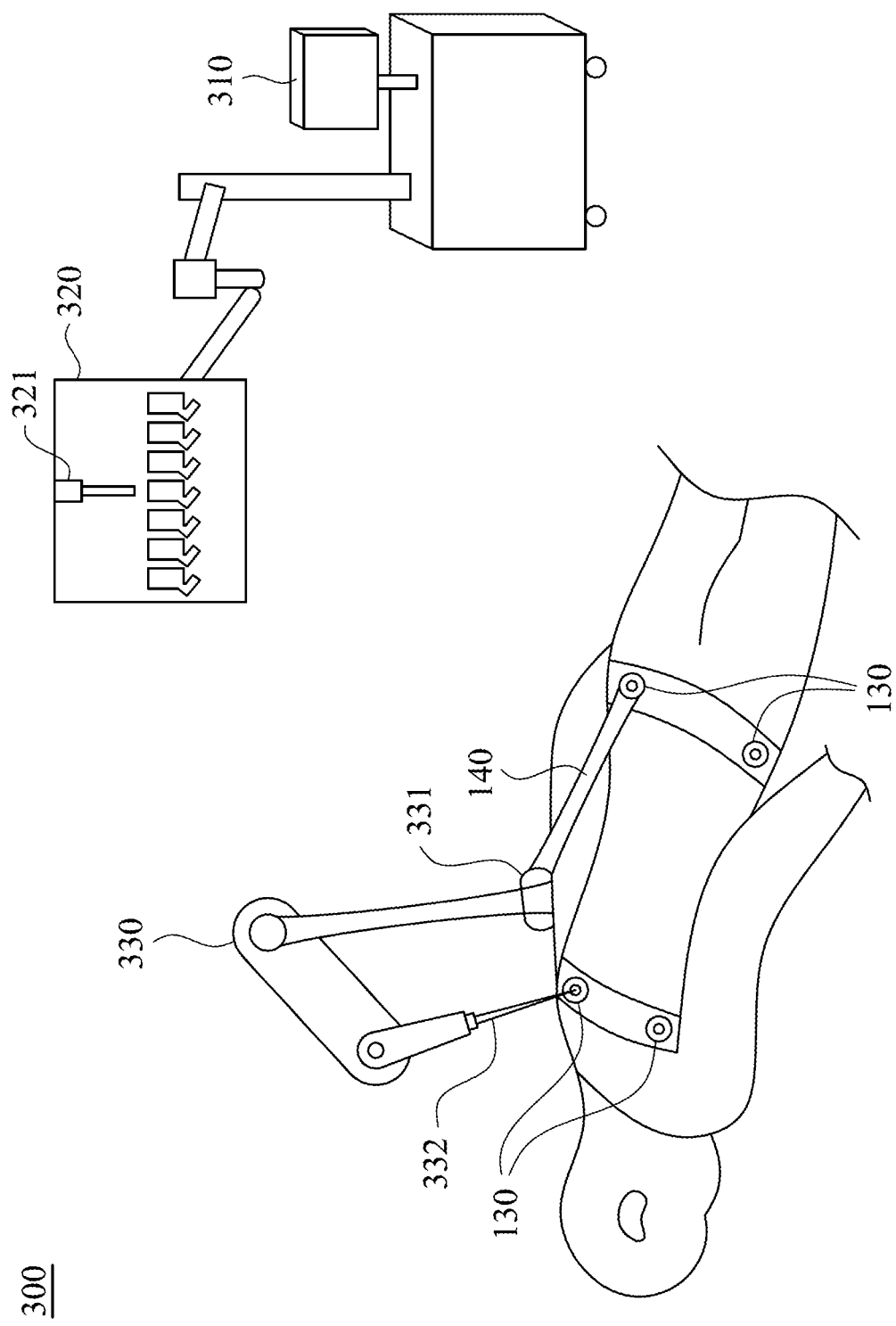
FIG. 3 is a schematic diagram of a system for registering the operating space in accordance with an embodiment.

In step 203, the back bracing is connected to the robotic arm. FIG. 3 is a schematic diagram of a system for registering the operating space in accordance with an embodiment. Referring to FIG. 2 and FIG. 3, a system 300 includes a computer system 310, a display 320, and a robotic arm 330. The computer system 130 is communicatively connected to the robotic arm 330. Instruments such as drills, files, scrapers, saws, screwdrivers or other tools that are commonly used in surgical operations to repair or remove parts of an anatomical area by drilling, grinding, cutting or scraping is disposed on the robotic arm 330. The robotic arm 330 can include, but not limited to, rotating joints, sliding joints, ball joints, universal joints, tube joints or any combination thereof to provide required degrees of freedom. A doctor can control the robotic arm 330 for surgery through a suitable device (for example, a controller with 6 degrees of freedom). The robotic arm 330 includes a base 331 which is used to connect to the back bracing. For example, the back bracing includes a rigid structure 140 which is used to connect to the base 331. As a result, the relative position between the back bracing and the robotic arm 330 will be fixed.

In step 204, the robotic arm is controlled to contact the positioning marks in an operating space (i.e. real world space). In the embodiment, the robotic arm 330 includes a tip 332. An operator can control the robotic arm 330 such that the tip 332 contacts each of the positioning marks 130, and the computer system 310 will obtain arm coordinates of each of the positioning marks 130 in an arm space (i.e. spaced used by the controller of the robotic arm) when the robotic arm 330 contacts the positioning marks 130. The arm coordinates are represented as a vector Y.

Figure 4:
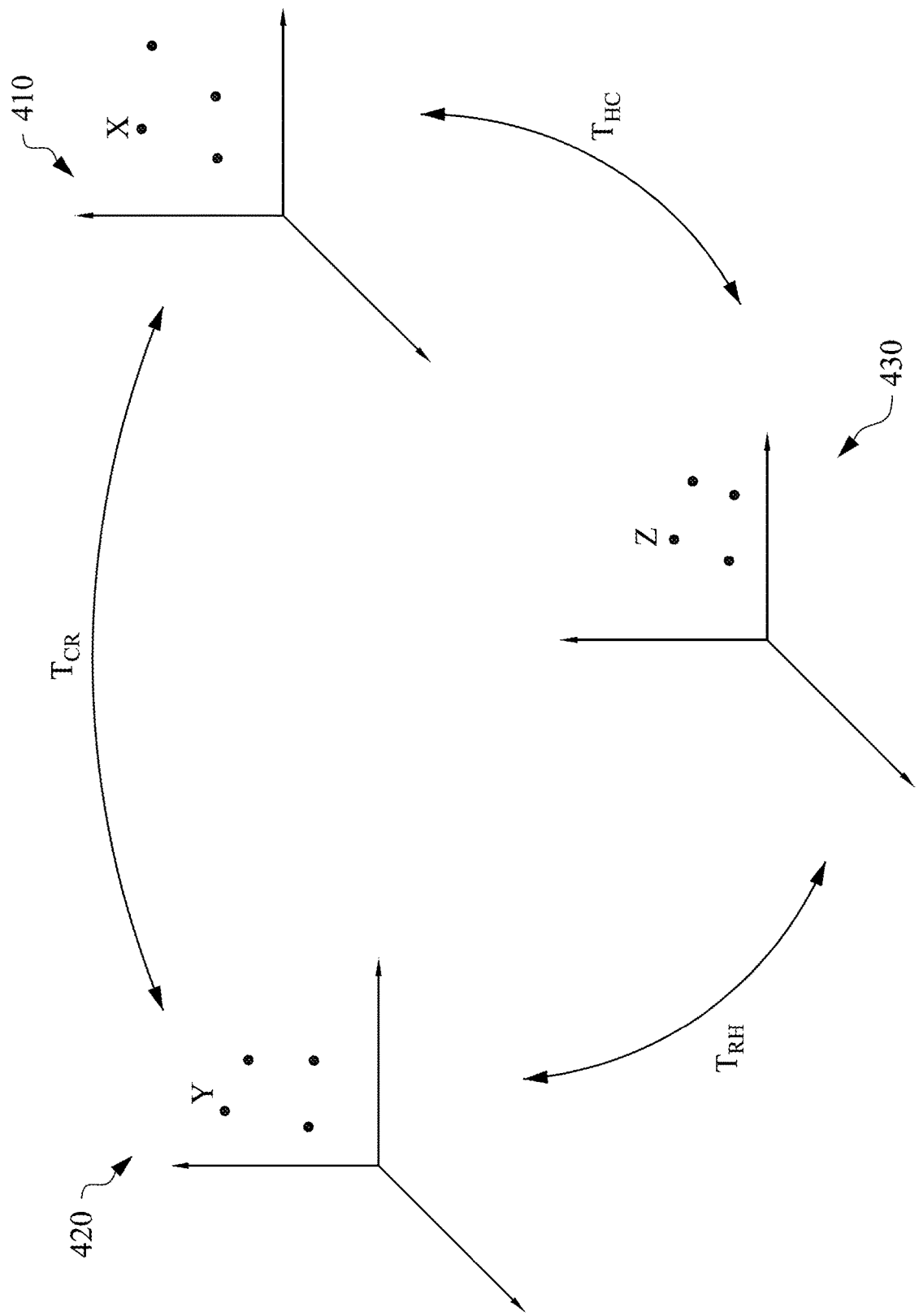
FIG. 4 is a schematic diagram of multiple spaces in accordance with an embodiment.

In step 205, conversion models among the image space, the operating space and the arm space are generated according to the image coordinates and the arm coordinates. Referring to FIG. 4 which is a schematic diagram of multiple spaces in accordance with an embodiment. There are three spaces, which are image space 410, arm space 420, and operating space 430 in the embodiment. The image coordinates X are in the image space 410. The arm coordinates Y are in the arm space 420. The operating space 430 is the real world space. The coordinates of the positioning marks 130 in the operating space 430 are represented as a vector Z. First, by matching the image coordinates X and the arm coordinates Y, a conversion model is computed between the image space 410 and the arm space 420. The conversion model is represented as a matrix $T_{CR}$ as the following equation (1).

$$X = T_{CR} Y \quad (1)$$

On the other hand, since the back bracing 100 is connected to the robotic arm 330 through the rigid structure 140, the position of the back bracing 100 is fixed. The positons of the positioning marks 130 relative to the back bracing 100 is known, and therefore a suitable reference, for example but not limited to a centroid position of the four positioning marks 130, can be taken as the original of the operating space 430 to compute the coordinates Z of the positioning marks 130 in the operating space 430. When the robotic arm 330 contacts the positioning marks 130, a conversion model, represented as a matrix $T_{RH}$, between the arm space 420 and the operating space 430 is computed in the following equation (2).

$$Y = T_{RH} Z \quad (2)$$

A conversion model, represented as a matrix $T_{HC}$, between the image space 410 and the operating space 430 is computed by substituting the equation (2) into the equation (1) as the following equation (3).

$$X = T_{HC} Z$$

$$T_{HC} = T_{CR} T_{RH} \quad (3)$$

In this way, the coordinates can be arbitrarily converted among the image space 410, the arm space 420 and operating space 430. Referring to FIG. 3 and FIG. 4, the computer system 310 can generate a navigation interface according to the conversion models by using any technology of virtual reality, augmented reality, alternative reality or mixed reality which is not limited in the disclosure. The navigation interface is shown on the display 320 in the embodiment, but the navigation interface may be shown on any head mounted device, tablet, or transparent display. For example, the computer system 310 can divide the spine in the CT image by an image process algorithm to generate virtual objects of vertebras that are shown on the navigation interface. The computer system 310 can transform a real-time arm position of the robotic arm 330 in the arm space 420 into a real-time image position in the image space 410 according to the conversion model $T_{CR}$, and then shows a virtual object 321 of the robotic arm 330 in the navigation interface. Accordingly, when the instrument on the robotic arm 330 enters the human body, the doctor can see the location of the instrument through the display 320. In the embodiment, the back bracing 100 helps fix the posture of the patient, and the back bracing 100 is connected to the robotic arm 330 through the rigid structure 140, and therefore the spine of the patient is not easily moved. Accordingly, the location of the spine is precisely shown on the navigation interface.

Figure 5:
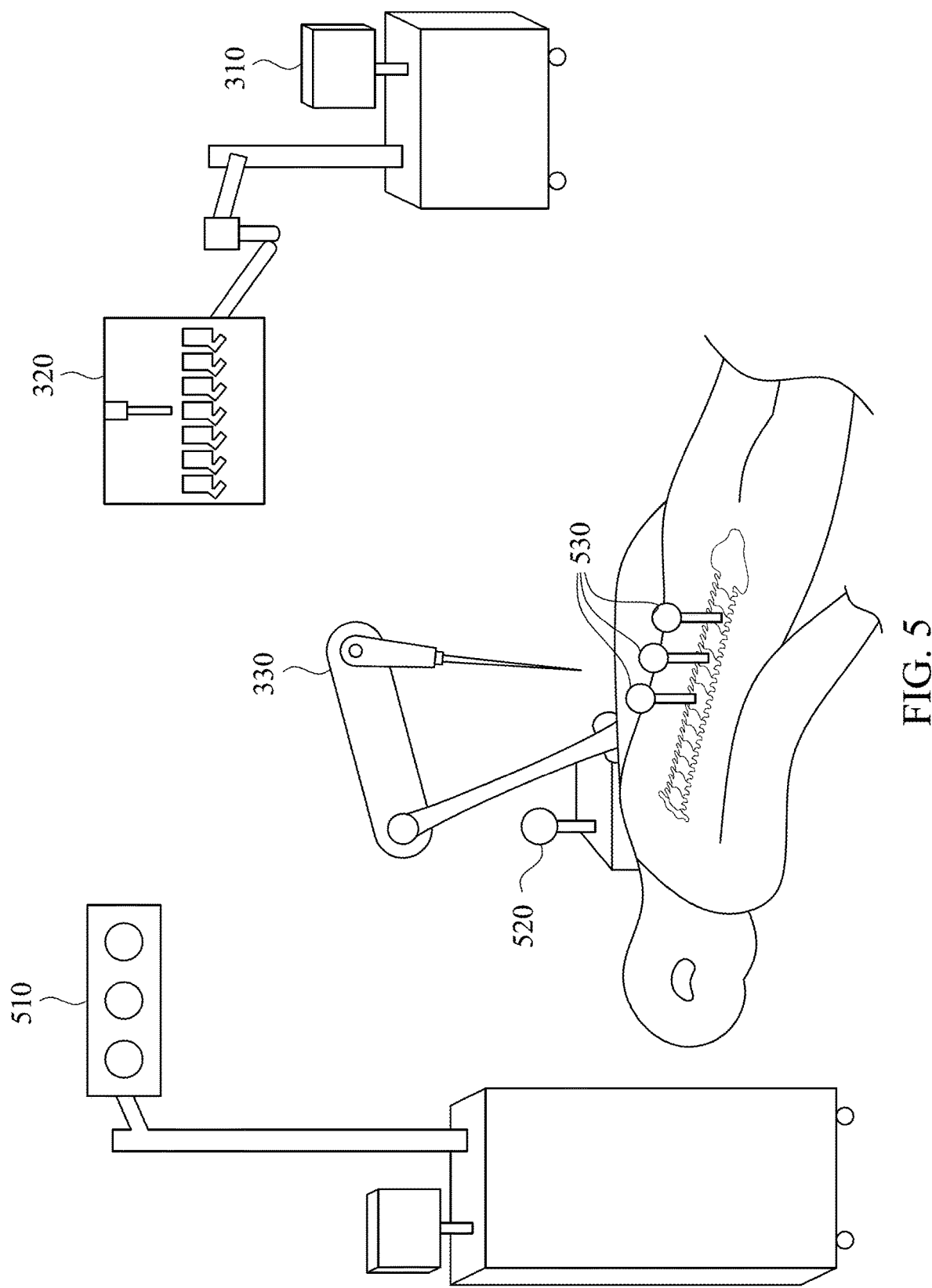
FIG. 5 is a schematic diagram of a system for registering the operating space in accordance with an embodiment.

FIG. 5 is a schematic diagram of a system for registering the operating space in accordance with an embodiment. In the embodiment of FIG. 5, the system further includes a camera 510, an arm positioning mark 520, and spine positioning marks 530. The spine positioning marks 520 are fixed on the patient's spine. For example, the spine positioning marks 530 are disposed on the vertebra to be operated. The arm positioning mark 520 is fixed on the robotic arm 330. The camera 510 captures images. In some embodiments, the camera 510 can include an infrared transmitter, an infrared sensor, dual cameras, a structured light sensing device or any device that can sense the depth of the scene. The computer system 310 recognizes the spine positioning marks 530 and the arm positioning mark 520 in the images to compute positions of the spine positioning marks 530 relative to the robotic arm 330. Accordingly, the computer system 310 can also show virtual objects of the spine positioning marks 520 on the display 320. In some embodiments, the back bracing 100 (not shown in FIG. 5 for simplification) is deformable. The camera 510 also captures images of the positioning marks 130. The computer system 310 can recognize the positioning marks 130 in the images to calibrate the position of the spine. For example, the computer system 310 can determine the shift of the positioning marks 130, and accordingly deforms the CT image. As a result, the CT image is adjusted based on the patient's posture.

The system is used for the spine surgery, but it may be used for a thoracic surgery or other suitable surgery. In other words, other steps may be inserted into the steps of FIG. 2.

In the disclosed system and method, the robotic arm, the CT image and the space of the patient's body are conveniently registered by using the back bracing.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for registering operating space, the system comprising:
   a back bracing comprising a plurality of positioning marks which are configured to be imaged in a computer tomography image, wherein the back bracing is configured to be worn by a patient;
   a computer system configured to recognize the positioning marks in the computer tomography image and compute image coordinates of the positioning marks in an image space; and
   a robotic arm comprising a base which is configured to connect to the back bracing in an operating space after the computer tomography image is generated, wherein the robotic arm is configured to contact the positioning marks in the operating space, and the computer system is configured to obtain arm coordinates in an arm space when the robotic arm contacts the positioning marks,
   wherein the computer system is further configured to generate at least one conversion model among the image space, the operating space, and the arm space according to the image coordinates and the arm coordinates.

2. The system of claim 1, wherein the back bracing comprises a plurality of straps which are configured to be tied onto a body portion the patient, and each of the positioning marks is disposed on one of the straps.

3. The system of claim 1, wherein the back bracing further comprises a rigid structure configured to connect to the base.

4. The system of claim 1, wherein the computer system is configured to provide a navigation interface, transform a real-time arm position of the robotic arm in the arm space into a real-time image position in the image space based on the at least one conversion model, and renders a virtual object of the robotic arm in the navigation interface according to the real-time image position.

5. The system of claim 1, further comprising a camera, a spine positioning mark, and an arm positioning mark, wherein the spine positioning mark is configured to be fixed on a spine of the patient, and the arm positioning mark is configured to be fixed on the robotic arm,
   wherein the camera is configured to capture an image, and the computer system is configured to recognize the spine positioning mark and the arm positioning mark in the image to compute a position of the robotic arm relative to the spine positioning mark in the operating space.

* * * * *